United States Patent [19]
Reiter et al.

[11] Patent Number: 5,149,865
[45] Date of Patent: Sep. 22, 1992

[54] NEW P-OXIBENZOIC ACID DERIVATIVES, PROCESS FOR THEIR PREPARATION AND THEIR USE AS DRUG

[75] Inventors: Friedemann Reiter, Putzbrunn; Helmut Grill, Vaterstetten; Hans-Helmut Henschel; Michael Schliack, both of Munich; Klaus Seibel, Gräfelfing; Roland Löser, Feldafing; Gerhard Lang, Freising, all of Fed. Rep. of Germany

[73] Assignee: Klinge Pharma GmbH, Munich, Fed. Rep. of Germany

[21] Appl. No.: 811,257

[22] Filed: Dec. 20, 1991

[30] Foreign Application Priority Data

Aug. 22, 1991 [DE] Fed. Rep. of Germany ....... 4127800

[51] Int. Cl.$^5$ .............................................. C07C 65/00
[52] U.S. Cl. .................................... 562/473; 560/64
[58] Field of Search .................... 562/473; 560/64; 514/568, 533, 544

[56] References Cited

U.S. PATENT DOCUMENTS

| 4,073,935 | 2/1978 | Grill et al. | 560/64 |
| 4,098,816 | 7/1978 | Thorne et al. | 562/473 |
| 4,154,850 | 5/1979 | Morgan | 560/64 |
| 4,713,472 | 12/1987 | van Sichle | 560/64 |
| 4,778,925 | 10/1988 | Grill | 562/473 |

FOREIGN PATENT DOCUMENTS

| 133935 | 7/1984 | European Pat. Off. |
| 1917540 | 11/1969 | Fed. Rep. of Germany |
| 1443339 | 4/1970 | Fed. Rep. of Germany |
| 7000858 | 10/1966 | Japan |

OTHER PUBLICATIONS

Siedel et al., J. Clin. Chem. Clin. Ciochem. *Improved Reagent for Enzymatic Determination of Serum Cholesterol*, 1981, No. 8, vol. 19, pp. 838–839.

Tiffany et al., Clin. Chem. *Clinical Evaluation of Kinetic Enzymatic Fixed-Time and Integral Analysis of Serum Triglycerides*, (1974) No. 4, vol. 20, pp. 476–481.

Dugan et al., Archives Bioch. Biophys. *Factors Affecting the Diurnal Variation in the Level of β-Hydroxy-β-Methylglutaryl* . . . , (1972) No. 1, vol. 152, pp. 21–27.

*Primary Examiner*—Paul J. Killos
*Attorney, Agent, or Firm*—Brumbaugh, Graves, Donohue & Raymond

[57] ABSTRACT

The invention relates to p-oxibenzoic acid derivatives of the general formula (1) where:

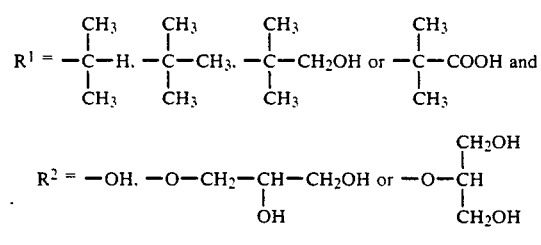

their diastereomers and enantiomers in pure form or as mixture of stereoisomeric forms and their physiologically compatible salts, a process for the preparation thereof and the use thereof for preparing drugs with hypolipemic effect.

13 Claims, No Drawings

NEW P-OXIBENZOIC ACID DERIVATIVES, PROCESS FOR THEIR PREPARATION AND THEIR USE AS DRUG

BACKGROUND OF THE INVENTION

DE-OS 3,326,164 and EP-A-0 133 935 discloses therapeutically valuable p-oxibenzoic acid derivatives of the general formula:

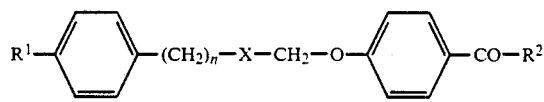

wherein:

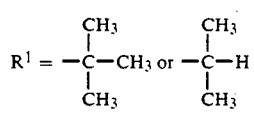

n = 1 or 2

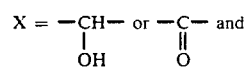

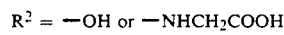

$R^2 =$ —OH or —NHCH$_2$COOH their physiologically compatible salts, process for the preparation thereof and use for preparing drugs with hypolipemic effect.

Furthermore, in German patent application P 40 32 037.5 p-oxibenzoic acid derivatives with hypolipemic properties are described which have the following formula:

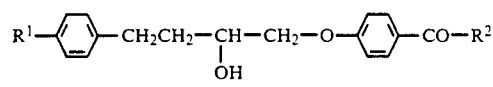

wherein

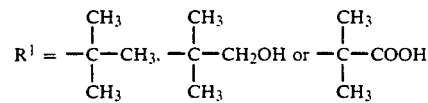

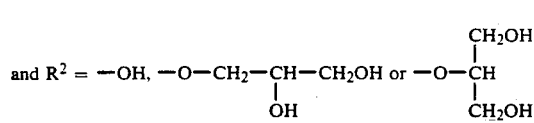

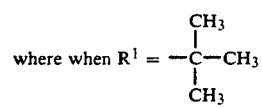

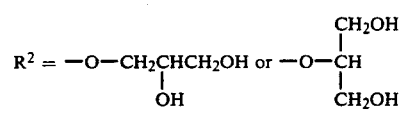

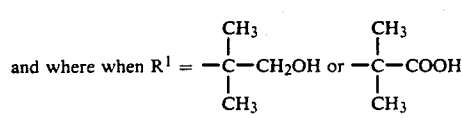

their physiologically compatible salts, process for the preparation thereof and their use for preparing drugs.

SUMMARY OF THE INVENTION

It has now surprisingly been found that with regard to their hypolipemic effect particularly advantageous p-oxibenzoic acid derivatives are those which differ essentially from the p-oxibenzoic acid derivatives known from DE-OS 3,326,164 and EP-A-0 133 935 and described in German patent application P 40 32 037.5 in that the aliphatic chain connecting the two aryl radicals has two hydroxy groups corresponding to the following graphic formula:

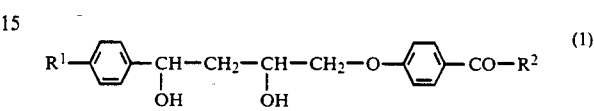

Accordingly, the subject of the invention is p-oxibenzoic acid derivatives of the general formula (1) wherein:

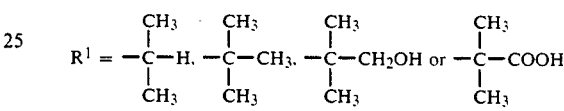

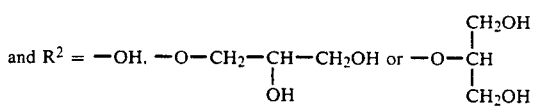

their diastereomers and enantiomers in pure form or as mixture of stereoisomeric forms and their physiologically compatible salts.

DETAILED DESCRIPTION OF THE INVENTION

Examples of compounds in accordance with the invention having the general formula (1) include the following p-oxibenzoic acid derivatives with particularly advantageous hypolipemic properties:

1) 1-(4'-tert. butylphenyl)-4-(4'-carboxyphenoxy)-butanediol-1,3;
2) 1-(4'-isopropylphenyl)-4-(4'-caraboxyphenoxy)-butanediol-1,3;
3) 1-[4'-(1,1-dimethyl-2-hydroxyethyl)-phenyl]-4-(4'-carboxyphenoxy)-butanediol-1,3;
4) 1-[4'-(1-carboxy-1-methylethyl)-phenyl]-4-(4'-carboxyphenoxy)-butanediol-1,3;
5) 1-(4'-tert.butylphenyl)-4-[4'-(2,3-dihydroxypropoxycarbonyl)-phenoxy]-butanediol-1,3;
6) 1-[4'-(1,1-dimethyl-2-hydroxyethyl)-phenyl]-4-[4'-(2,3-dihydroxypropoxycarbonyl)-phenoxy]-butanediol-1,3.

The preparation of the p-oxibenzoic acid derivatives according to the invention can take place in that in a manner known per se epoxides of the general formula (2)

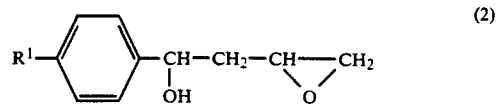

in which

-continued

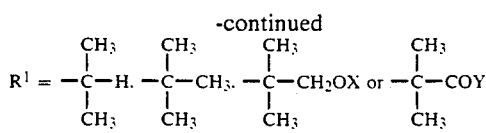

and both X and Y denote a suitable protective group, are reacted with the corresponding p-oxibenzoic acid esters, the esters obtained possibly saponified, possibly present protective groups split off and the diastereomer mixture obtained possibly separated, the separation taking place before or after splitting the protective group off.

The diastereomers may be separated by conventional methods, advantageously by fractional crystallization or chromatographically.

X may for example be a tetrahydropyranyl group and Y a tetrahydropyranyloxy group or an alkoxy group, in particular short-chain alkoxy group, for example a methoxy group.

The reaction of the epoxides with the p-oxibenzoic acid esters may take place in a solvent, for example dimethyl formamide, in the presence of alkali, for example in the form of the alkali salt of the p-oxibenzoic acid ester used, at elevated temperature, for example 80° to 130° C.

The epoxides necessary for carrying out the process of the invention and having the general formula (2) may be obtained by a procedure in which an aldehyde of the general formula (3)

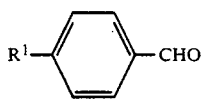

(3)

in which $R^1$ has the meaning indicated, is reacted with an allyl magnesium halide, for example allyl magnesium bromide, to give a phenyl butene 3-ol-1 of the following formula (4)

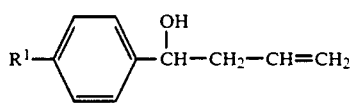

(4)

whereupon the compound contained is transformed in a manner known per se by oxidation, for example by means of an organic peracid, for example meta-chloroperbenzoic acid (MCPBA), into the epoxide of the following formula (5):

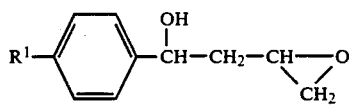

(5)

The epoxide is obtained in the form of the diastereomer mixture with two enantiomer pairs which is then reacted in the manner indicated with a corresponding p-oxibenzoic acid ester.

For example, the preparation of 1-(4'-tert. butylphenyl)-4-(4'-carboxyphenoxy)-butanediol-1,3 is carried out in that (1) 4-tert. butylbenzaldehyde is reacted with an allyl magnesium halide, for example allyl magnesium bromide, to 1-(4'-tert. butylphenyl) butene-3-ol-1, that (2) the 1-(4'-tert. butylphenyl) butene-3-ol-1 obtained is oxidized to 1-(4'-tert. butylphenyl)-3,4-epoxy-butanol-1, that (3) the 1-(4'-tert. butylphenyl)-3,4-epoxy-butanol-1 obtained is reacted with 4-hydroxybenzoic acid methyl ester to form a 1-(4'-tert. butylphenyl)-4-(4'-methoxycarbonylphenoxy)butanediol-1,3-diastereomer mixture, that (4) the diastereomers are separated from each other and (5) the separated esters are saponified with alkaline.

For the therapeutic use as hypolipemic drugs the new compounds of the general formula (1) and their salts are preferably orally administered. Generally, the oral daily dose for adults is 0.1 to 5 g, preferably 0.3 to 2 g.

The active substances can be galenically processed in the usual manner for the oral administration. Suitable as pharmaceutical carrier substances are conventional auxiliary substances such as lactose, saccharose, mannite, potato or maize starch, cellulose derivatives or gelatins, possibly with addition of lubricants, for example magnesium or calcium stearate, and polyethylene glycols.

The invention will be explained in detail with reference to the example of the preparation of 1-(4'-tert.-butylphenyl)4-(4'-carboxyphenoxy)-butanediol-1,3 and the pharmacodynamic effects thereof.

1-(4'-tert.butylphenyl)-butene-3-ol-1

To a solution of 123 ml (0.123 mole) allyl magnesium bromide solution (1M in diethyl ether), the solution of 16.2 g (0.100 mole) 4-tert.butylbenzaldehyde in 50 ml abs. ether is added dropwise under a nitrogen atmosphere at 10° C., stirring carried out for 2 hours at 10°-15° C. and the mixture left to stand over night at room temperature. 50 ml 25% NH4Cl solution are then stirred in whilst cooling, the phases separated and the aqueous phase extracted several times with methyl-tert-.butylether. The combined organic phases are washed with water and dried over $Na_2SO_4$. After extracting the solvent under vacuum, a yellowish liquid remains which is reacted without further purification. Yield 19.5 g (96%).

$^1$H-NMR-spectra (60 MHz; CDCl$_3$):

| 1.33 | s | (9) | (CH$_3$)$_3$C |
| 2.23 broad | s | (1) | OH (exchangeable) |
| 2.30–2.60 | m | (2) | CHCH$_2$CH |
| 4.48–4.83 | t | (1) | ArCH |
| 4.83–5.30 | m | (2) | =CH$_2$ |
| 5.47–6.30 | m | (1) | =CH |
| 7.10–7.50 | m | (4) | Aromat |

The NMR spectra are taken at 60 or 100 MHz. The chemical shifts are given in ppm with respect to TMS ($\delta$=0.0) and the relative intensities are added in brackets. s=singlet; d=doublet; dd=double doublet; t=triplet; q=quartet; m=multiplet.

1-(4'-tert butylphenyl)-3,4-epoxy-butanol-1
(Diastereomer mixture)

Whilst cooling with ice, 18.9 g (0.093 mole) 85% MCPBA are added to the solution of 19.0 g (0.093 mole) 1-(4'-tert.butylphenyl)-butene-3-ol-1 in 100 ml dichloromethane and stirring then carried out for 5 hours at room temperature. Thereafter, the suspended chlorobenzoic acid is extracted, the filtrate washed free of acid with dilute NaOH and neutrally with water and dried over $Na_2SO_4$. After withdrawing the solvent in vacuum a yellow oil (21 g) remains which is chromatographically purified with chloroform using silica gel. Yield: 13 g (59%).

$^1$H-NMR-spectrum (60 MHz; CDCl$_3$):

| 1.28 | s | (9) | (CH$_3$)$_3$ |
|---|---|---|---|
| 1.47–2.13 | m | (2) | CHCH$_2$CH |
| 2.25–3.30 | m | (4) | CH——CH$_2$ \O/ |
| 2.97 | broad s | | OH |
| 4.57–5.02 | m | (1) | ArCH |
| 7.00–7.53 | m | (4) | Aromat |

1-(4′-tert.butylphenyl)-4-(4′-methoxycarbonylphenoxy)-butanediol-1,3 a) Preparation of the diastereomer mixture 22.0 g (0.100 mole) 1-(4′-tert.butylphenyl)-3,4-epoxybutanol-1, 15.2 g (0.100 mole) 4-hydroxybenzoic acid methyl ester and 0.85 g (0.005 mole) 4-hydroxybenzoic acid methyl ester sodium salt are dissolved in 85 ml dimethyl formamide and stirred for 12 hours at 100° C. After cooling the reaction mixture, it is poured into iced water and extracted twice with ethyl acetate. The purified organic phases are washed with water and dried over Na$_2$SO$_4$. After extracting the solvent in vacuum the raw diastereomer mixture remains as brown resinous residue; raw yield 36.8 g (99%).

b) Separation of the diastereomers

The raw product is subjected to a fractional crystallization from chlorobutane. The first crystal fractions contain strongly enriched the diastereomer A which in thin-film chromatography with silica gel with chloroform/ethyl acetate 90/10 (v/v) as mobile solvent has the higher R$_f$ value. It is further purified by repeated crystallization from chlorobutane. Colorless crystals with melting point 121°–122° C.

$^1$H-NMR spectrum (100 MHz; CDCl$_3$)

| 1.31 | s | (9) | (CH$_3$)$_3$C |
|---|---|---|---|
| 1.90–2.13 | m | (2) | CH—CH$_2$—CH |
| 3.07 | d | (1) | OH (exchangeable) |
| 3.59 | d | (1) | OH (exchangeable) |
| 3.87 | s | (3) | OCH$_3$ |
| 3.96 | d | (2) | CH$_2$O |
| 4.30 | m | (1) | CHOH |
| 5.01 | m | (1) | ArCH |
| 6.85–8.01 | m | (8) | Aromat |

The residue of the mother liquor is freed from impurities by chromatography with silica gel and chloroform/ethyl acetate 90/10 (V/V) and the diastereomer mixture thus being purified, thereafter again subjected to a fractional crystallization from chlorobutane. The first crystal fractions represent mixtures and the subsequent ones contain greatly enriched the diastereomer B with the smaller R$_f$ value. They are purified by crystallization from diisopropyl ether/chlorobutane in the ratio 100/10, 90/20 and finally 75/35. Colorless crystals with melting point 103°–106° C.

$^1$H-NMR spectrum (110 MHz; CDCl$_3$):

| 1.31 | s | (9) | (CH$_3$)$_3$C |
|---|---|---|---|
| 2.00 | m | (2) | CHCH$_2$CH |
| 2.87 | d | (1) | OH |
| 3.09 | d | (1) | OH |
| 3.87 | s | (3) | OCH$_3$ |
| 4.00 | d | (2) | OCH$_2$ |
| 4.29 | m | (1) | CHOH |
| 5.06 | m | (1) | ArCH |
| 6.85–8.01 | m | (8) | Aromat |

1-(4′-tert.butylphenyl)-4-(4′-carboxyphenoxy)-butanediol-1,3;

Diastereomer A 3.72 g (0.010 mole) 1-(4′-tert.butylphenyl)-4-(4′-methoxycarbonylphenoxy)-butanediol-1,3, diastereomer A, are boiled with 1.65 g (0.025 mole) 85% KOH in 30 ml methanol and 5 ml water for 6 hours with weak reflux. After cooling the solution is diluted with water, acidified with concentrated HCl and the product extracted twice with ethyl acetate. The purified organic phases are washed with water and dried over Na$_2$SO$_4$. After extraction of the solvent in vacuum a crystalline residue remains which is recrystallized from acetonitrile/methanol (7/1). Yield 2.98 g (83%); colorless crystals with melting point 164°14 166° C.

C$_{21}$H$_{26}$O$_5$(358.4).

Molar mass 358 (determined with mass spectroscope by electron impact ionization (70ev)).

| IR-spectrum (KBr): | ν (OH) | 3600–2400 cm$^{-1}$ |
|---|---|---|
| | ν (C=O) | 1680 cm$^{-1}$ |
| $^1$H-NMR spectrum (100 MHz; CDCl$_3$/CD$_3$OD): | | |
| 1.31 | s | (9) | (CH$_3$)$_3$C |
| 1.90–2.10 | m | (2) | CHCH$_2$CH |
| 3.87–4.33 | m | (6) | CHCH$_2$O, 3 OH |
| 4.96 | dd | (1) | ArCH |
| 6.80–8.10 | m | (8) | Aromat |

1-(4′-tert.butylphenyl)-4-(4′-carboxyphenoxy)-butanediol-1,3:

Diastereomer B

In the manner described above for diastereomer A, 1-(4′-tert.butylphenyl)-4-(4′-methoxycarbonylphenoxy)-butanediol-1,3, diastereomer B, is saponified with alkaline. The vitreous raw product crystallizes from acetonitrile. Yield 91%; colorless crystals with melting point 140°–143° C.

C$_{21}$H$_{26}$O$_5$(358.4).

Molar mass 358 (mass spectroscopy).

| IR-Spectrum (KBr): | V(OH) | 3600–2400 cm$^{-1}$ |
|---|---|---|
| | V(C=O) | 1680 cm$^{-1}$ |
| $^1$H-NMR spectrum (100 MHz; CDCl$_3$/CD$_3$OD): | | |
| 1.31 | s | (9) | (CH$_3$)$_3$C |
| 1.98 | m | (2) | CHCH$_2$CH |
| 3.80–4.40 | m | (6) | CHCH$_2$O, 3 OH |
| 4.99 | dd | (1) | ArCH |
| 6.80–8.10 | m | (8) | Aromat |

In corresponding manner, the following compounds according to the invention can for example be prepared:
(a) 1-(4′-isopropylphenyl)-4-(4′-carboxyphenoxy)-butanediol -1,3;
(b) 1-[4′-(1,1-dimethyl-2-hydroxyethyl)-phenyl]-4-(4′-carboxyphenoxy)-butanediol-1,3;
(c) 1-[4′-(1-carboxy-1-methylethyl)-phenyl]-4-(4′-carboxyphenoxy)-butanediol-1,3;

(d) 1-(4'-tert.butylphenyl)-4-[4'-(2,3-dihydroxypropoxycarbonyl)-phenoxy]-butanediol-1,3;

(e) 1-[4'-(1,1-dimethyl-2-hydroxyethyl)-phenyl]-4-[4'-(2,3-dihydroxypropoxycarbonyl)-phenoxy]-butanediol-1,3.

Pharmacodynamic Effects of
1-(4'-tert.butylphenyl)-4-(4'-carboxyphenoxy)-butanediol-1,3: Diastereomer A and
1-(4'-tert.butylphenyl)-4-(4'-carboxyphenoxy)-butanediol-1,3: Diastereomer B 1) Determination of the hypolipidemic effect on rats The superiority of the compounds claimed over the clofibrate used in therapy for a long time can be demonstrated clearly by the lipid-reducing effect.

The lipid-reducing effect of the test substances was examined on groups each of 10 normolipemic male Wistar rats weighing 200 to 220 g.

The tests were carried out after a 3-week retraining of the eating habits of the animals. The controlled feeding was carried out daily from 8 a.m. to 10 a.m. The test substances were administered at 11 a.m.

The test compounds were absorbed in an aqueous solution of 0.25% agar and 0.84% sodium chloride and administered orally. After three administrations over a period of 3 days blood was extracted from the animals. Cholesterol and triglycerides were determined in the serum with the aid of the "Cobas-Bio" centrifugal analyzer of Hoffmann-La Roche:

Methods a) Cholesterol determination

CHOD-PAP method, enzymatic color test according to J. Siedel et al. (J. Clin. Chem. Clin. Biochem. 19, 838 (1981))

b) Triglyceride determination

Enzymatic cleavage of the triglycerides with the aid of special lipases with subsequent determination of the liberated glycerol according to T. O. Tiffany et al. (Clin. Chem. 20, 476 (1974))

TABLE 1

Percentage change of total cholesterol (TC) and Triglyceride (TG) level in the rat serum after oral administration of the test substances

| Compound number | Dose (mg/kg) | TC X ± SD | % Change TG X ± SD |
|---|---|---|---|
| Comparative subs. Clofibrate | 100 | −14.5 + 12.0 | −29.2 + 19.4 |
| Diastereomer A | 100 | −39.1 ± 15.5 | −26.4 ± 13.1 |
| Diastereomer B | 100 | −66.9 ± 8.6 | −29.7 ± 15.5 |

2) Determination of the inhibition of cholesterol synthesis 3 g freshly prepared rat liver were homogenized in 6 ml ice-cooled buffer and centrifuged at 20000 * g for 20 minutes. The supernatant was separated off and used for the following determinations.

10 μl of the methanolic test substance solution was pipetted into a mixture of 110 μl supernatant and 300 μl incubation solution and incubated at 37° C. for 20 minutes. Thereafter, 10 μl of a $^{14}C$ acetate solution was pipetted in and incubated for a further 30 minutes. Thereafter, 500 μl ethanolic KOH solution was added to the mixture, further incubated for 60 minutes at 75° C. and thereafter the reaction stopped by cooling in an ice bath. To enable a yield correction to be made for the subsequent extraction of the $^{14}C$ cholesterol forming, $^{3}H$ cholesterol ($\approx 10^{-3}$) was added by pipetting. In addition, 500 μl of an ethanolic solution of cold cholesterol was added. The cholesterol of the mixture was extracted twice with 1 ml petroleum ether, the extract concentrated by evaporating to dryness and taken up in 0.6 ml of an ethanol acetone mixture (1/1). The dissolved cholesterol was then precipitated by means of 1.4 ml of a digitonin solution (=7 mg). After 15 hours at 0° C. the precipitate was centrifuged off, dissolved with 0.5 ml methanol/glacial acetic acid (33/5) and diluted with two ml methanol. The radioactivity of the resulting cholesterol was then determined in 12 mm scintillation liquid (Dimilume) by means of a scintillation counter.

Solutions employed

Buffer: 6.8 g $KH_2PO_4$, 0.6 g $MgCl_2$, 0.37 g EDTA, 1.83 g nicotine amide, 51.35 g saccharose and 0.44 ml mercaptoethanol were dissolved in distilled water and diluted to 500 ml ($P_H = 7.2$)

Incubation solution: The following were dissolved, in each case individually:

8.6 mg AND with 1.3 ml buffer
10.2 mg NADP with 1.3 ml buffer
39.6 mg glucose-6-phosphate with 0.65 ml buffer
31.6 μl glucose-6-phosphate dehydrogenase (1000 U/0.9 ml) with 0.285 buffer These solutions were not mixed until immediately prior to use.

$^{14}C$-acetate: Solution: 250 μCi $^{14}C$-Na-acetate was dissolved by means of 1 ml distilled water, Solution 2: 512.5 mg Na-acetate was dissolved in 10 ml distilled water.

Before the test, 0.1 ml of solution 1 and 0.4 ml of solution 2 were mixed and then mixed with 2 ml distilled water.

Ethanolic KOH: 10 g were dissolved in 100 ml ethanol.

Method: R. E. Dugan et al. Archives Bioch. Biophys. 152 21, (1972)

TABLE 2

Percentage inhibition of cholesterol biosynthesis in rat liver homogenate by the test substances

| Diastereomer | Concentration (Mole/l) | % Control |
|---|---|---|
| A | $3*10^{-7}$ | 122 |
| A | $1*10^{-6}$ | 103 |
| A | $3*10^{-6}$ | 97 |
| A | $1*10^{-5}$ | 36 |
| A | $3*10^{-5}$ | 14 |
| A | $1*10^{-4}$ | 9 |
| A | $3*10^{-4}$ | 2 |
| B | $1*10^{-5}$ | 42 |

We claim:
1. p-oxibenzoic acid derivatives of the general formula (1)

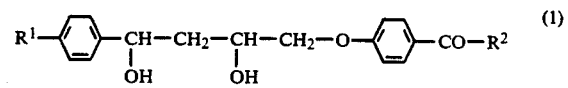

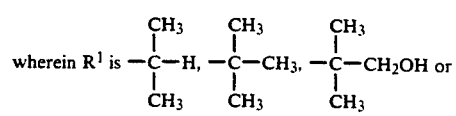

-continued

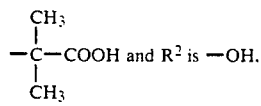

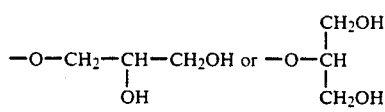

or a physiologically compatible salt thereof.

2. 1-(4'-tert.butylphenyl)-4-(4'-carboxyphenoxy)-butanediol-1,3 in the form of its two separate diastereomers, in the form of a diastereomer mixture or as pure enantiomers.

3. A p-oxibenzoic acid derivative according to claim 1, wherein the derivative has a single stereoisomeric form.

4. A p-oxibenzoic acid derivative according to claim 1 comprising a mixture of two or more stereoisomers.

5. Process for the preparation of a p-oxibenzoic acid derivative of the formula

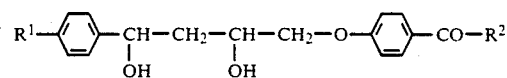

wherein

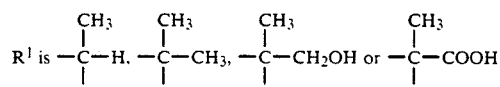

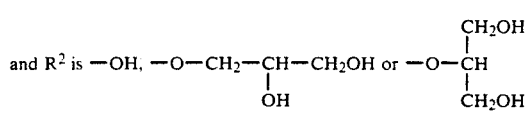

comprising reacting an epoxide of the general formula

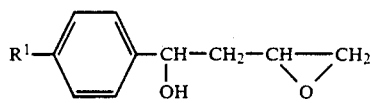

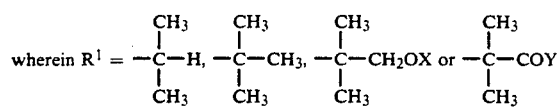

and both X and Y denote a protective group with a p-oxibenzoic acid ester of the formula

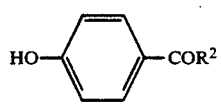

to form a diastereomeric product.

6. Process according to claim 3 for the preparation of 1-(4'-tert.-butylphenyl)-4-(4'-carboxyphenoxy)-butanediol-1,3, wherein (1) 4-tert.-butylbenzaldehyde is reacted with an allyl magnesium halide to form 1-4'-tert.-butylphenyl)-butene-3-ol-1, (2) the 1-(4'-tert.-butylphenyl)-butene-3-ol-1 obtained is oxidized to 1-(4'-tert.-butylphenyl)3,4-epoxy-butanol-1, (3) the 1-(4'-tert.-butylphenyl)-3,4-epoxy-butanol-1 obtained is reacted with 4-hydroxybenzoic acid methyl ester to form a 1-(4'-tert.-butylphenyl)-4-(4'-methoxycarbonylphenoxy)butanediol-1,3-diastereomer mixture, (4) the diastereomers are separated from each other and (5) the separated esters are saponified with alkaline.

7. A process according to claim 5, further comprising the step of separating the diastereomeric product into individual stereoisomeric products.

8. Process according to claim 6 wherein the diastereomers are separated by fractional crystallization.

9. A pharmaceutical composition comprising a p-oxibenzoic acid derivative of the formula

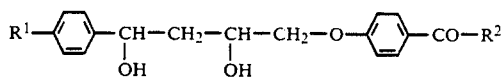

wherein

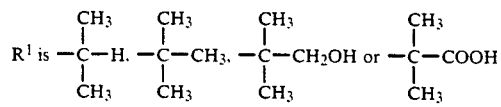

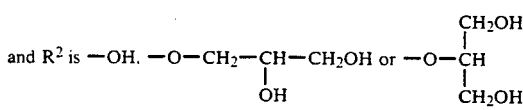

in an amount effective to have a hypolipemic effect and a pharmaceutically acceptable carrier.

10. A pharmaceutical composition according to claim 6, wherein the p-oxibenzoic acid derivative is 1-(4'-tert.-butylphenyl)-4-(4'-carboxyphenoxyl)-butanediol -1,3.

11. A method of reducing serum lipids in a patient comprising administering to the patient an effective amount of a p-oxibenzoic derivative of the formula

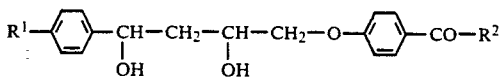

wherein

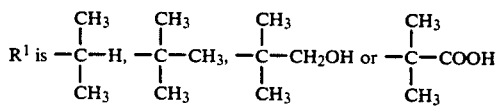

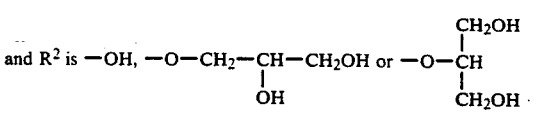

or a pharmaceutically acceptable salt thereof.

12. A method according to claim 11, wherein the p-oxibenzoic acid derivative is administered orally at a level of 0.1 to 5.0 grams per day.

13. A method according to claim 11, wherein the p-oxibenzoic acid derivative is 1-(4'-tert.-butylphenyl)-4-(4'-carboxyphenoxyl)-butanediol-1,3.

* * * * *

UNITED STATES PATENT AND TRADEMARK OFFICE
CERTIFICATE OF CORRECTION

PATENT NO. : 5,149,865

DATED : September 22, 1992

INVENTOR(S) : Reiter et al.

It is certified that error appears in the above-identified patent and that said Letters Patent is hereby corrected as shown below:

On the title page, item [56] References Cited, under "OTHER PUBLICATIONS" "Ciochem" should read -- Biochem--.

Col. 6, line 25, "164°14 166°C." should read --164°-166°C.--;

Col. 7, line 48, "X" (both instances) should read --$\overline{X}$--;

Col. 7, line 49, "+" (both instances) should read --$\pm$--;

Col. 8, line 25, "AND" should read --NAD--;

Col. 8, line 39, "10 g were" should read --10 g KOH were--;

Col. 10, line 5, "3,4-" should read -- -3,4- --;

Col. 10, line 17, "claim 6" should read --claim 7--;

Col. 10, lines 39-40, "claim 6" should read --claim 9--.

Signed and Sealed this

Twenty-eighth Day of September, 1993

Attest:

BRUCE LEHMAN

*Attesting Officer*     *Commissioner of Patents and Trademarks*